US00PP36399P2

(12) United States Plant Patent
Heuger

(10) Patent No.: US PP36,399 P2
(45) Date of Patent: Jan. 14, 2025

(54) ***HELLEBORUS* PLANT NAMED 'HG 1412'**

(50) Latin Name: ***Helleborus ericsmithii* X *Helleborus* x *hybridus***
Varietal Denomination: HG 1412

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,515

(22) Filed: Nov. 14, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Helleborus* plant named 'HG 1412', characterized by its upright to somewhat outwardly spreading and mounded plant habit; vigorous growth habit; dark green-colored leaflets with lighter green-colored venation; freely flowering habit; purplish red-colored flowers; and good garden performance.

1 Drawing Sheet

Figure 2:
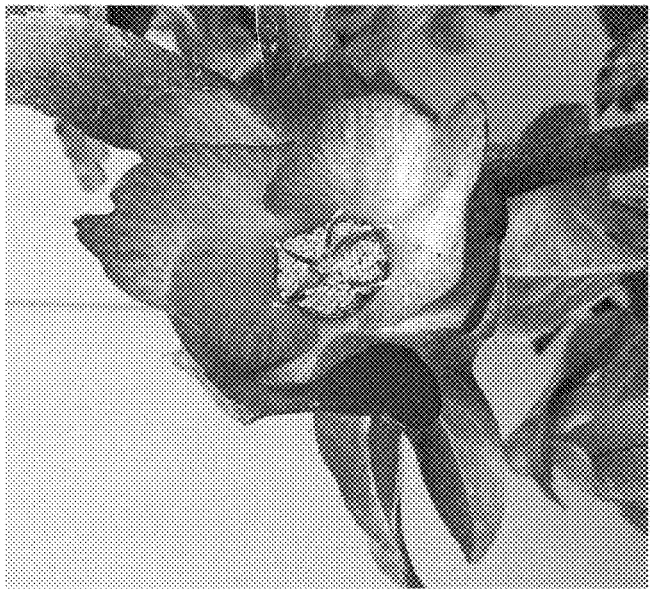

Botanical designation: *Helleborus ericsmithii* X *Helleborus* x *hybridus.*
Cultivar denomination: 'HG 1412'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Dec. 1, 2022, application number 2022/2738. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus ericsmithii* X *Helleborus* x *hybridus* and hereinafter referred to by the name 'HG 1412'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in January 2016 of a proprietary selection of *Helleborus ericsmithii* identified as code number P472, not patented, as the female, or seed, parent and a proprietary selection of

*Helleborus* x *hybridus* identified as code number O1485, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December 2017.

Asexual reproduction of the new *Helleborus* plant by in vitro axillary meristem culture in a controlled environment in Glandorf, Germany since April 2018 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HG 1412'. These characteristics in combination distinguish 'HG 1412' as a new and distinct *Helleborus* plant:

1. Upright to somewhat outwardly spreading and mounded plant habit.
2. Vigorous growth habit.
3. Dark green-colored leaflets with lighter green-colored venation.
4. Freely flowering habit.
5. Purplish red-colored flowers.
6. Good garden performance.

Plants of the new *Helleborus* differ from plants of the female parent selection in the following characteristics:

1. Leaflets of plants of the new *Helleborus* are lighter green in color than leaflets of plants of the female parent selection.

2. Flowers of plants of the new *Helleborus* are lighter purplish red in color than flowers of plants of the female parent selection.

Plants of the new *Helleborus* differ from plants of the male parent selection in the following characteristics:

1. Leaflets of plants of the new *Helleborus* are darker green in color than leaflets of plants of the male parent selection.
2. Flowers of plants of the new *Helleborus* are lighter purplish red in color than flowers of plants of the male parent selection.

Plants of the new *Helleborus* can also be compared to plants of *Helleborus* x *ericsmithii* X *Helleborus* x *hybridus* 'COSEH 4100', disclosed in U.S. Plant Pat. No. 28,296. In side-by-side comparisons, plants of the new *Helleborus* differ primarily from plants of 'COSEH 4100' in flower color as flowers of plants of the new *Helleborus* are purplish red in color whereas flowers of plants of 'COSEH 4100' are red purple to greyed purple in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

Figure 1:
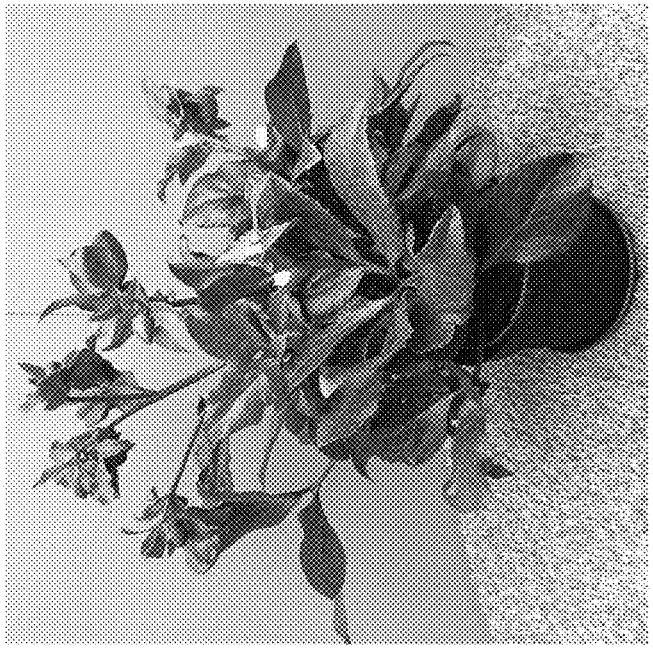

The photograph at the left of the sheet (FIG. 1) is a side perspective view of a typical flowering plant of 'HG 1412' grown in a container.

The photograph at the right of the sheet (FIG. 2) is a close-up view of a typical flowering plant of 'HG 1412'.

DETAILED BOTANICAL DESCRIPTION

The aforementioned photographs and following observations, measurements and values describe plants grown during the early spring in 15-cm containers in a glass-covered greenhouse in Glandorf, Germany and under cultural practices typical of commercial *Helleborus* production. During the production of the plants, day temperatures ranged from 12 C to 32 C and night temperatures ranged from 5 C to 12 C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus ericsmithii* X *Helleborus* x *hybridus* 'HG 1412'.

Parentage:

*Female, or seed, parent*.—Proprietary selection of *Helleborus ericsmithii* identified as code number P472, not patented.

*Male, or pollen, parent*.—Proprietary selection of *Helleborus* x *hybridus* identified as code number O1485, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held above the foliar plane; plant shape, roughly flattened globular; vigorous growth habit and moderate to rapid growth rate.

*Plant height, soil level to top of foliar plane*.—About 26.3 cm.

*Plant height, soil level to top of flowers*.—About 47.8 cm.

*Plant diameter* (*area of spread*).—About 71 cm.

Leaf description:

*Arrangement*.—Leaves arranged in a basal rosette; leaves palmately compound with typically five leaflets per leaf.

*Leaf length*.—About 18 cm.

*Leaf width*.—About 18.7 cm.

*Leaflet length*.—About 11.6 cm.

*Leaflet width*.—About 6.2 cm.

*Leaf shape*.—Palmate; roughly reniform in outline.

*Leaflet shape*.—Elliptic to broadly elliptic.

*Leaflet apex*.—Acute.

*Leaflet base*.—Attenuate.

*Leaflet margin*.—Serrate; moderately coarsely undulate.

*Leaflet texture and luster, upper surface*.—Smooth, glabrous; coriaceous and tough; moderately glossy.

*Leaflet texture and luster, lower surface*.—Smooth, glabrous; coriaceous and tough; slightly glossy.

*Leaflet venation pattern*.—Pinnate and reticulate.

*Leaflet color*.—Developing leaflets, upper surface: Close to a blend of NN137A and 147A; midvein, proximally, close to 187A. Developing leaflets, lower surface: Close to a blend of 148A and 197A; midvein, close to a blend of N186C and 187A. Fully developed leaflets, upper surface: Close to a blend of NN137A and 147A; venation, close to 144A, proximally, tinged with close to 200A. Fully developed leaflets, lower surface: Close to 147B; venation, close to 178A.

*Petioles*.—Length: About 17.5 cm. Diameter: About 6 mm by 7.5 mm. Strength: Strong. Texture and luster, upper and lower surfaces: Smooth, glabrous; slightly glossy. Color, upper and lower surfaces: Close to 146B; moderately to heavily covered with fine dots and stripes, close to 166A.

Flower description:

*Flower shape and habit*.—Single rotate bowl-shaped flowers arranged in panicles; freely flowering habit with about six to ten flowers per inflorescence and about 110 flowers and flower buds per plant; flowers face mostly outwardly to slightly nodding and moderately upwardly.

*Fragrance*.—None detected.

*Natural flowering season*.—Plants begin flowering about ten months after planting; plants flower naturally during the late winter into the early spring in Germany.

*Flower longevity on the plant*.—About ten days; sepals persistent, other flower parts are not persistent.

*Flower buds*.—Length: About 2.4 cm. Diameter: About 1.3 cm. Shape: Ovate. Texture and luster: Smooth, glabrous; matte. Color: Upper surface, close to a blend of 59B and 187C; lower surface, close to 182B tinged with close to N148B.

*Inflorescence height* (*including peduncle*).—About 51.8 cm.

*Inflorescence diameter*.—About 22.6 cm.

*Flower diameter*.—About 6.1 cm.

*Flower depth*.—About 2.7 cm.

*Petals*.—All petals are transformed into nectaries.

*Sepals*.—Quantity and arrangement: About five, arranged in a single whorl. Length: About 3.8 cm. Width: About 3.2 cm. Shape: Broadly ovate; slightly to moderately concave. Apex: Obtuse to bluntly acute. Base: Truncate to obtuse. Margin: Entire; coarsely undulate. Texture and luster, upper surface: Smooth, glabrous; matte. Texture and luster, lower surface: Smooth, glabrous; slightly glossy. Color: When opening, upper surface: Close to a blend of N77B and 183D; towards the center and base, close to 144B. When opening, lower surface: Close to 185B and 187C; venation, close to 187B. Fully opened, upper surface: Close to a blend of 60C and N77B; towards the base, tinged with close to 144B; at the base, sparsely covered with fine dots, close to 187C; venation, similar to lamina colors; color does not change with subsequent development. Fully opened, lower surface: Close to 187C to 187D; venation, close to 187A to 187B; color does not change with subsequent development.

*Flower bracts*.—Quantity per flower: Typically one or two. Length: About 4.5 cm. Width: About 2.9 cm. Shape: Ovate. Apex: Acute to cleft or three-lobed with acute tips. Base: Truncate to obtuse. Margin: Proximally, entire; distally, finely serrate; slightly coarsely undulate. Color, upper surface: Close to NN137A; towards the base, close to 138A to 138B. Color, lower surface: Close to 147A strongly tinged with close to N186C; midvein, close to N186C.

*Peduncles*.—Length: About 37.3 cm. Diameter: About 7.5 mm to 9 mm. Aspect: About 25 degrees from vertical. Strength: Strong. Texture and luster: Smooth, glabrous; moderately glossy. Color: Close to N186C; heavily covered with fine dots, close to 146D.

*Pedicels*.—Length: About 3.6 cm. Diameter: About 2.5 mm. Aspect: About 35 degrees from peduncle axis. Strength: Moderately strong. Texture and luster: Smooth, glabrous; moderately glossy. Color: Close to 187A; moderately covered with fine dots, close to 147D.

*Reproductive organs*.—Stamens: Quantity per flower: About 60. Filament length: About 1.6 cm. Filament color: Close to 157C to 157D. Anther shape: Double and broadly reniform; basifixed. Anther size: About 1.75 mm by 2.5 mm. Anther color: Close to 154D. Pollen amount: Sparse. Pollen color: Close to 4D. Pistils: Quantity per flower: About six, occasionally five or eight. Pistil length: About 1.4 cm. Stigma diameter: About 0.3 mm. Stigma shape: Club-shaped. Stigma color: Close to 158D. Style length: About 1.35 cm. Style color: Close to between 184B and 185B. Ovary color: Close to 149A; adaxial rib, slightly tinged with close to 182C. Nectaries (transformed petals): Quantity per flower: About 11 or 12. Length: About 1.2 cm. Diameter: About 5 mm. Shape: Tubular, flattened; apices, obtuse. Texture and luster, inner and outer surfaces: Smooth, glabrous; slightly glossy. Color, immature, inner and outer surfaces: Close to 144B; towards the apex, close to N144A. Color, mature, inner surface: Close to N144A; towards the apex, close to 153C; with subsequent development, color becoming closer to N144B and towards the apex, close to 172B. Color, mature, outer surface: Close to N144A; towards the apex, close to 153C; with subsequent development, color becoming closer to N144B and towards the apex, close to 172B and at the base, close to N144A.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35 C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HG 1412' as illustrated and described.

* * * * *